United States Patent [19]

Armstrong et al.

[11] Patent Number: 4,768,950
[45] Date of Patent: Sep. 6, 1988

[54] ORTHODONTIC ELASTOMERIC LIGATURE MANIPULATOR

[75] Inventors: Maclay M. Armstrong, Seattle; Steven A. Houser, Edmonds, both of Wash.

[73] Assignee: Unitek Corporation, Monrovia, Calif.

[21] Appl. No.: 741,666

[22] PCT Filed: Aug. 13, 1984

[86] PCT No.: PCT/US84/01297

§ 371 Date: Apr. 12, 1985

§ 102(e) Date: Apr. 12, 1985

[87] PCT Pub. No.: WO85/00743

PCT Pub. Date: Feb. 28, 1985

Related U.S. Application Data

[63] Continuation-in-part of Ser. No. 523,830, Aug. 15, 1983, abandoned.

[51] Int. Cl.$^4$ .............................. A61C 3/00
[52] U.S. Cl. ............................ 433/3; 433/4
[58] Field of Search ............ 433/4, 3, 141, 159, 433/162, 157; 81/302; 128/354; 7/168, 167

[56] References Cited

U.S. PATENT DOCUMENTS

| | | | |
|---|---|---|---|
| 955,955 | 4/1910 | Engelsman | 81/43 |
| 1,100,486 | 6/1914 | Merliss | 81/302 |
| 1,346,584 | 7/1920 | Angle | 433/4 |
| 1,355,790 | 10/1920 | Young | 433/4 |
| 1,363,534 | 12/1920 | Rogers | 433/3 |
| 1,974,106 | 9/1934 | Gardella | 128/354 |
| 3,475,818 | 11/1969 | Abrams | 433/3 |
| 4,001,940 | 1/1977 | Cusato | 433/3 |
| 4,106,374 | 8/1978 | Dragan | 81/302 |
| 4,310,305 | 1/1982 | Frajdenrajch | 433/4 |
| 4,392,494 | 7/1983 | Ashby | 433/4 |
| 4,462,404 | 7/1984 | Schwarz et al. | 128/354 |
| 4,553,932 | 11/1985 | Armstrong et al. | 433/4 |

FOREIGN PATENT DOCUMENTS

| | | |
|---|---|---|
| 523365 | 10/1953 | Belgium. |
| 764150 | 12/1956 | United Kingdom. |
| 921015 | 3/1963 | United Kingdom. |

Primary Examiner—John J. Wilson
Attorney, Agent, or Firm—Robert W. Beach; Ward Brown

[57] ABSTRACT

A head (9) projecting from the end of a rod body (1') or from the apex of a flat trifurcated quadrant body (1) has an offset fixed prong (10) projecting from its end which is crossed by a movable prong (22) carried by a rocker (20) mounted on the head and tiltable to alter the spacing between the prongs. The tip portions (13 and 25) of the prongs have notches (14 and 26) facing away from each other to hold a ligature ring (37) in stretched condition for application to the wings (44 and 45) of an orthodontic tooth bracket (39). The tip portions of the prongs are canted relative to the prong shanks to be disposed in parallel planes and a line passing through the notches is at an angle to one edge of the body. The notch (26) in the movable prong (22) is deeper than the notch (14) in the stationary prong (10) and the portion of the shallower notch (14) adjacent to the tip of the prong forms the prong tip as a probe. A spring (28) presses the rocker to urge the tip of the movable prong away from the tip of the fixed prong.

46 Claims, 11 Drawing Sheets

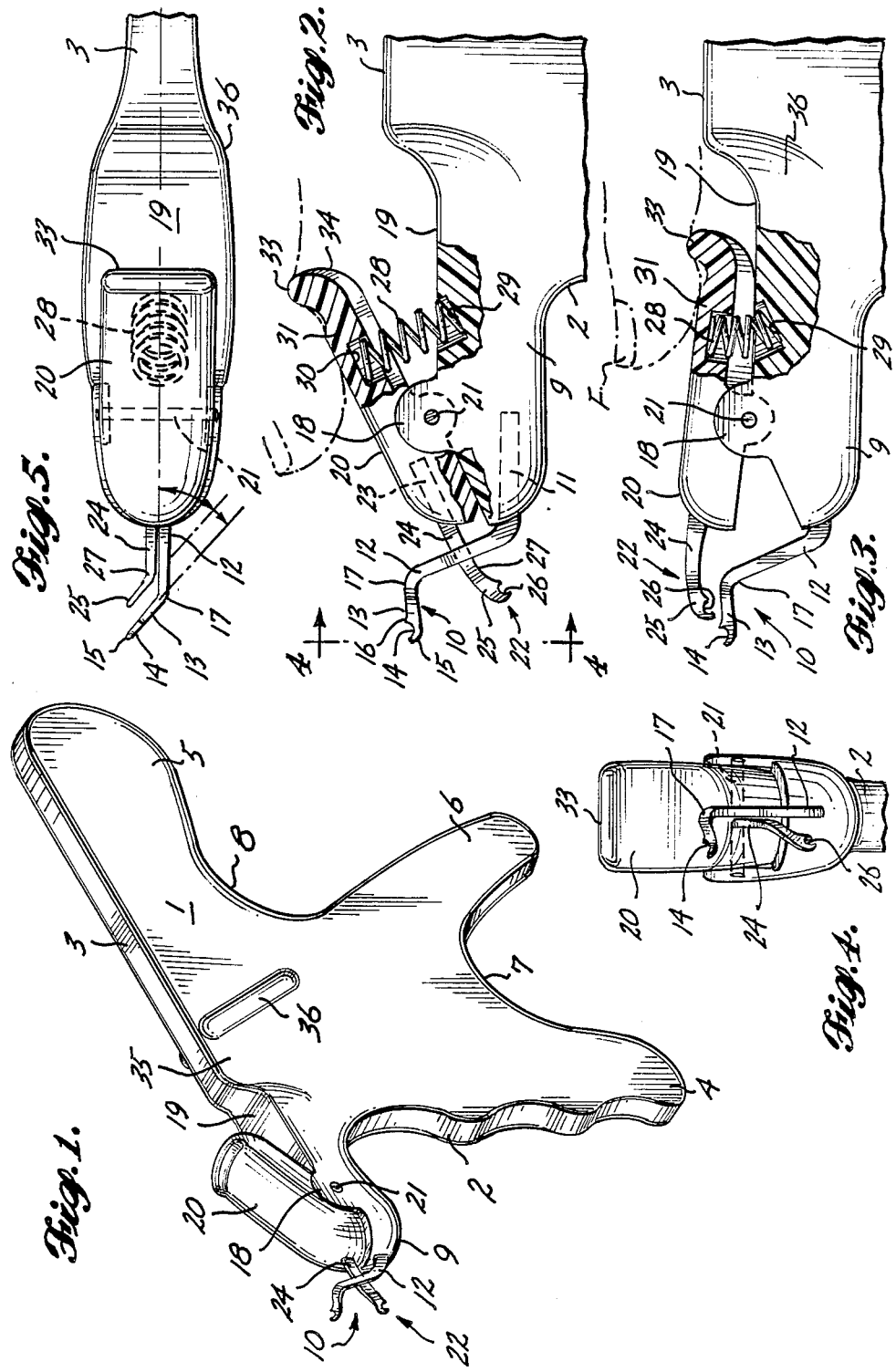

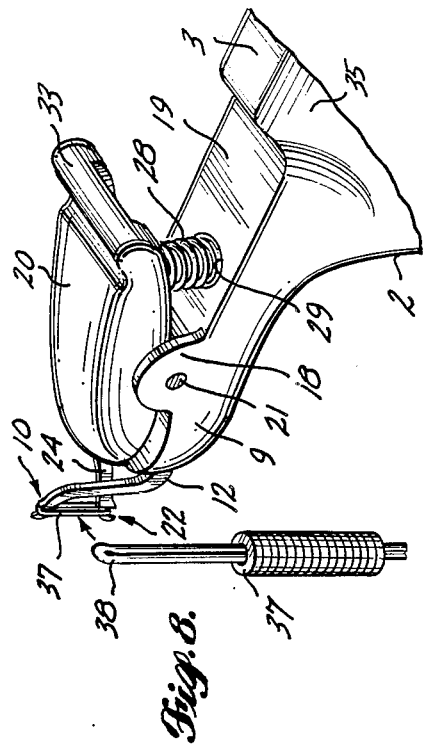
Fig. 6.
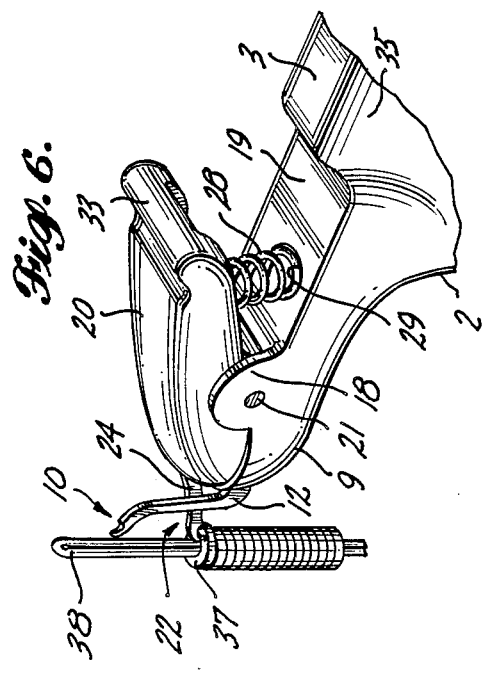
Fig. 8.
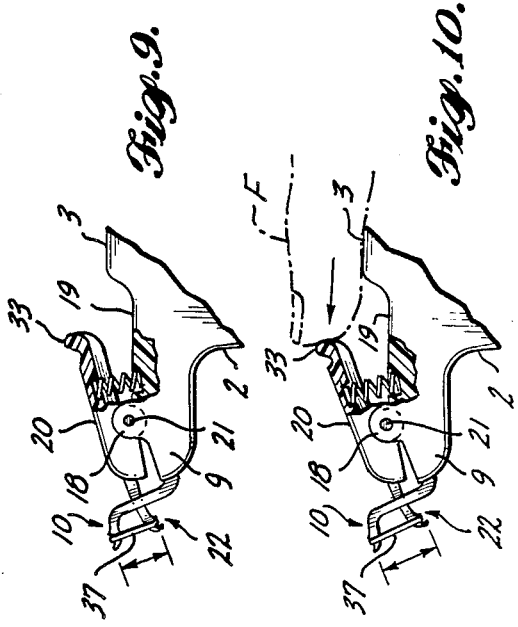
Fig. 9.
Fig. 10.
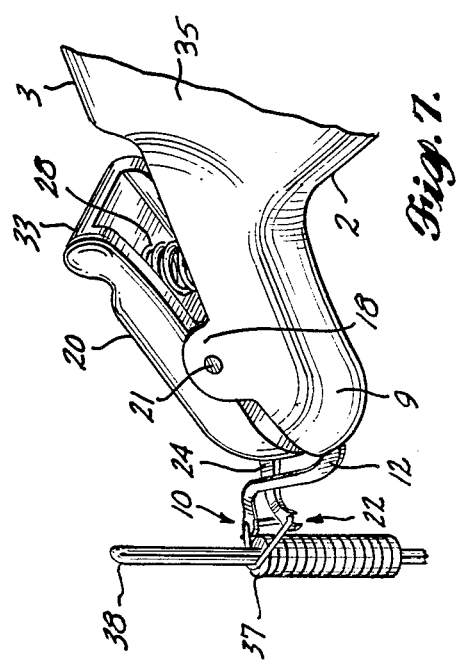
Fig. 7.

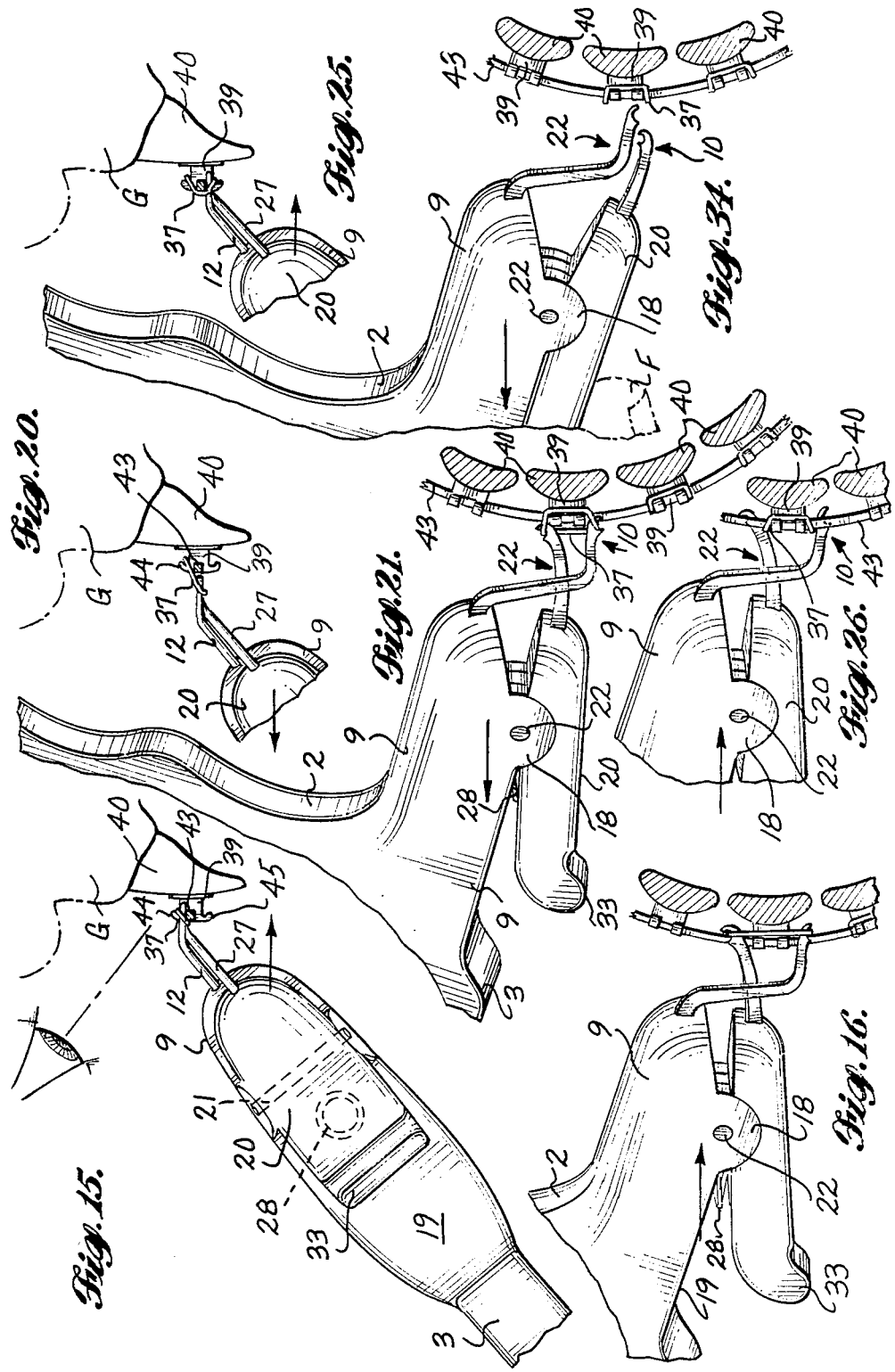

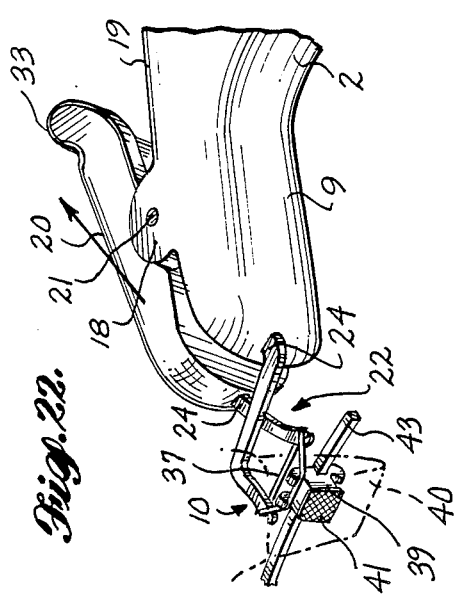
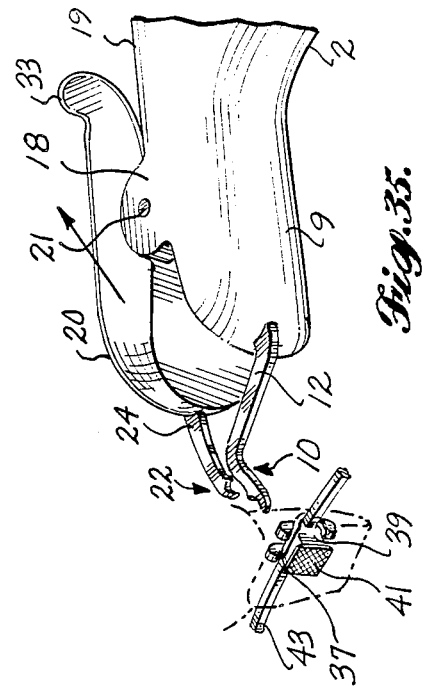
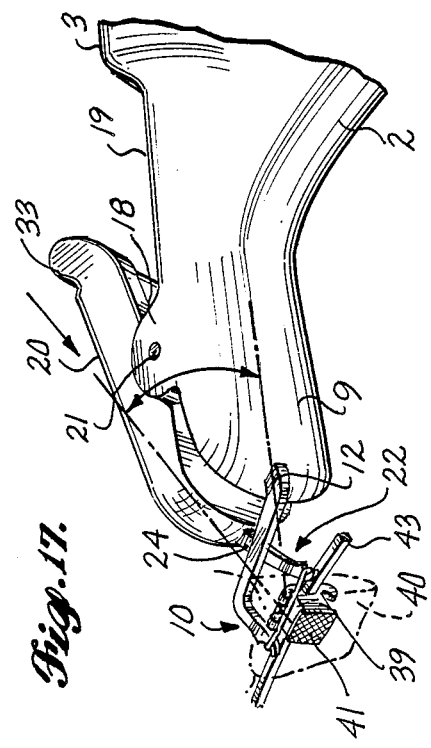
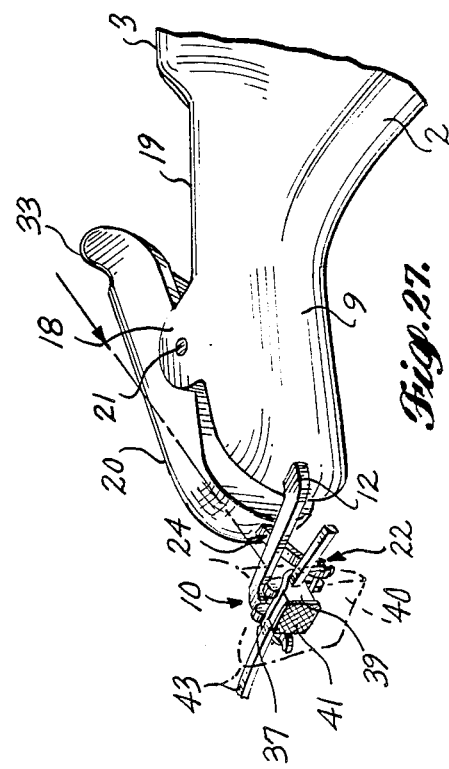

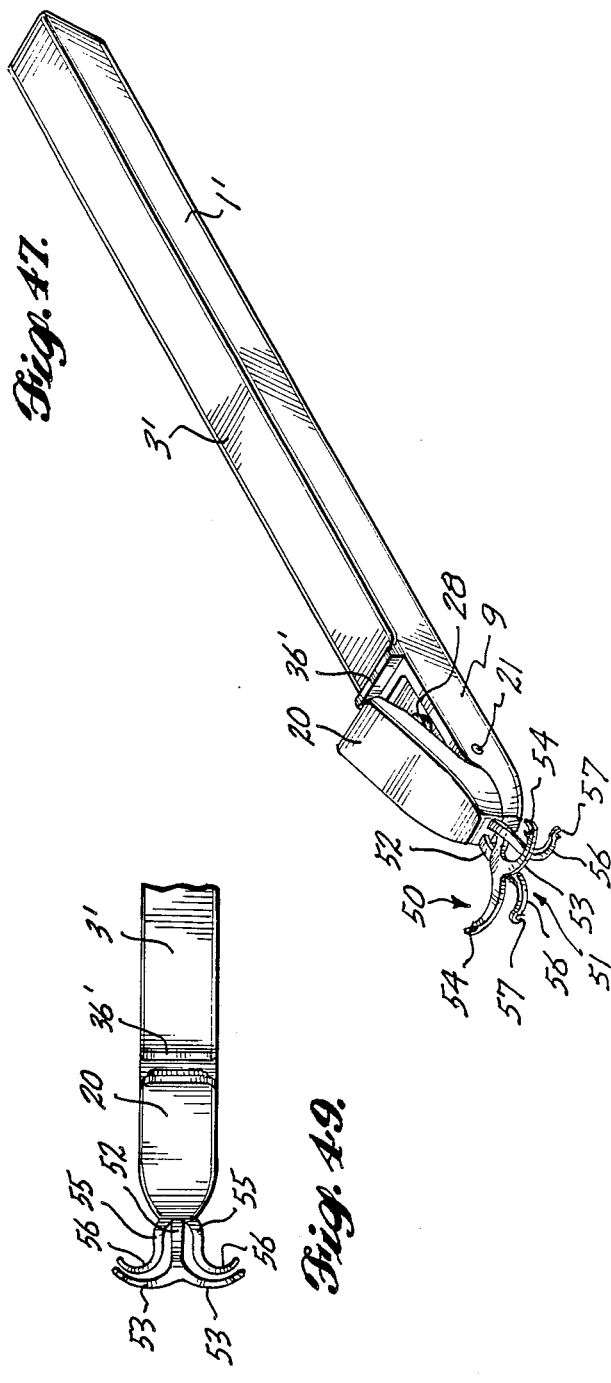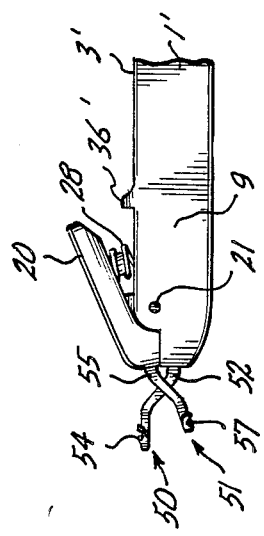

ORTHODONTIC ELASTOMERIC LIGATURE MANIPULATOR

CROSS REFERENCE

This application is a continuation-in-part of copending U.S. application Ser. No. 523,830, filed Aug. 15, 1983, now abandoned in the names of Steven A. Houser and Maclay M. Armstrong for Orthodontic Elastomeric Ligature Manipulator.

TECHNICAL FIELD

This invention relates to a manipulator for orthodontic elastomeric ligatures of the ring type, or which include a ring component, and can be utilized for applying such a ligature to the wings of an orthodontic tooth bracket for the purpose of holding an arch wire in the slot between such wings, and for removing such a ligature ring from tooth bracket wings.

BACKGROUND ART

Elastomeric ligature ring appliers proposed or available heretofore have been of two principal types, namely, the pliers-type and the tweezers-type. Both of these types are represented in Cusato U.S. Pat. No. 4,001,940, issued Jan. 11, 1977, the tweezers-type being shown in FIGS. 1 to 5, 5A and 6, and the pliers-type being shown in FIGS. 14 to 21.

Patents showing previous pliers-type of apparatus cited against the application resulting in the aforesaid U.S. Pat. No. 4,001,940 are Belgian Pat. No. 523,365 of October 1953, United Kingdom Pat. No. 764,150 of December 1956 and United Kingdom Pat. No. 921,015 of March 1963. Prior patents showing tweezers-type apparatus cited against the application resulting in U.S. Pat. No. 4,001,940 are Engelsman U.S. Pat. No. 955,955, issued Apr. 26, 1910, and Gardella U.S. Pat. No. 1,974,106, issued Sept. 18, 1934.

Patents issued later than U.S. Pat. No. 4,001,940 showing pliers-type of apparatus are Dragan U.S. Pat. No. 4,106,374, issued Aug. 15, 1978, and Frajdenrajch U.S. Pat. No. 4,310,305, issued Jan. 12, 1982.

The pliers-type of device includes jaws that are spring-pressed toward each other having tips that can be inserted into the aperture of an elastomeric ligature ring element after which the pliers handles can be pressed toward each other to spread the tips and thereby stretch and hold the ligature ring between the tips. U.S. Pat. No. 4,001,940 in FIGS. 17 and 18 provides a latch that can be engaged between the handle elements of the pliers to hold such elements in contracted position for maintaining the tips in spread condition to hold a ring stretched.

The tips of a tweezers-type of device are normally urged apart by the resiliency of the tweezers and the tips can be pressed together for engagement with a ligature ring and then released to spread and hold the ring. Such tweezers may have a latch to hold the legs of the tweezers apart for maintaining a ring in stretched condition, as shown in the Engelsman U.S. Pat. No. 955,955.

It is difficult to stretch and hold an elastomeric ring in stretched condition by manipulation of a pliers-type instrument when applying such a ring to the wings of an orthodontic bracket, and it is also difficult to manipulate latch mechanism for holding apart the jaws of such a pliers instrument and for releasing the jaws from a ligature ring. Moreover, such latch mechanism is intended to hold the pliers jaws spaced apart only a predetermined distance, whereas it may be desirable to stretch ligature rings different amounts depending on the type of bracket to which the ring is to be applied.

The tweezers-type of ring-holding instrument is difficult to hold firmly in the hand, and it is more difficult to hold such an instrument securely while manipulating latch mechanism to hold the legs of the tweezers in spaced relationship.

DISCLOSURE OF THE INVENTION

In accordance with the present invention, a manipulator has a body that can be grasped between the thumb and one or more fingers of a hand, and such body may be flat and furcated to provide one or more throats or crotches into which the web of the hand between the thumb and forefinger can be fitted as the manipulator is grasped. The body of such manipulator carries a fixed prong projecting from it and an adjacent movable prong which prongs can engage, stretch and hold a ligature ring between them while the manipulator is manipulated to apply such ligature ring to the wings of an orthodontic tooth bracket. The shanks of the prongs may be crossed and their tip portions may be canted relative to their shanks in parallel relationship and offset from the handle to enable the body of the manipulator and the operator's hand grasping it to be held out of the operator's line of sight to the ring as it is applied to tooth bracket wings. Also the tips may be arranged at an angle relative to the body to improve vision and facilitate holding and manipulation of the manipulator. The tip portions of the prongs have notches opening away from each other for cradling opposite sides of a ligature ring, one notch being relatively deep and the other notch being relatively shallow and located in its prong tip portion sufficiently close to the prong tip as to shape the end of such tip as a generally straight probe.

Advantages of the manipulator of the present invention are that is is easy to hold securely in the hand and can be manipulated conveniently to apply ligature rings to the ears or wings of an orthodontic bracket, even though the orthodontic brackets are of different widths, which brackets may be on teeth in various portions of a mouth.

A further advantage is that the applicator can be used to apply ligature rings to tooth brackets without applying substantial pressure or torque to the tooth bracket or arch wire which can cause patient discomfort.

BRIEF DESCRIPTION OF DRAWINGS OF THE PREFERRED EMBODIMENT

The details of the invention will be described in connection with the accompanying drawings of my preferred embodiment in which, FIG. 1 is a top perspective of the manipulator, FIG. 2 is an enlarged fragmentary side elevation of the head portion of the manipulator with parts broken away, FIG. 3 is a side elevation similar to FIG. 2 but with parts shown in a different relationship, FIG. 4 is an end elevation of the head portion of the manipulator viewed from line 4—4 of FIG. 2, FIG. 5 is a plan of the head portion of the manipulator, FIGS. 6, 7 and 8 are top perspectives of the head portion of the manipulator illustrating sequential conditions of the manipulator in picking an elastomeric ligature ring from a ring storage or supply spindle, FIGS. 9 and 10 are side elevations of the head portion of the manipulator holding a ring stretched to different degrees, FIG. 11 is a detail plan and FIG. 12 is a detail elevation of the tip portions of manipulator prongs on an enlarged scale illustrating an initial positioning of a ring alongside a tooth bracket, FIG. 13 is a plan and FIG. 14 is an elevation of the tip portions of the manipulator prongs corresponding to FIGS. 11 and 12, respectively, but showing the prongs in a sequential position for applying a ring to wings of a tooth bracket,

FIG. 15 is a plan,

FIG. 16 is a side elevation and

FIG. 17 is a perspective of the head portion of the manipulator shown executing the step illustrated by FIGS. 13 and 14 in applying a ring to tooth bracket wings.

FIG. 20 is a plan,

FIG. 21 is an elevation and

Figure 18:
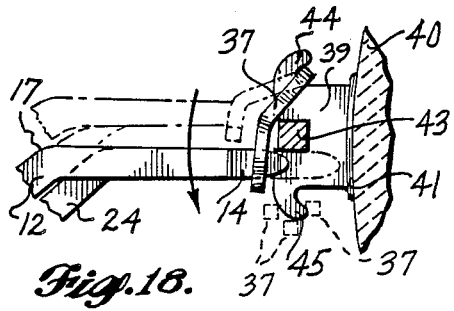
FIG. 18 is a plan and FIG. 19 is an elevation of the tip portions of the manipulator prongs illustrating a further sequential step in applying a ligature ring to the wings of an orthodontic tooth bracket.
Figure 19:
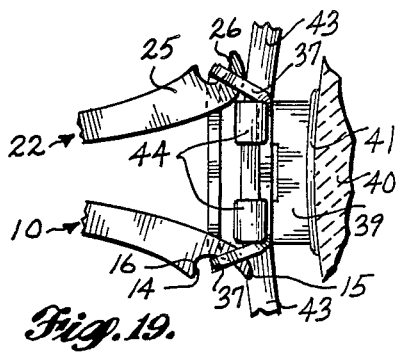
Figure 23:
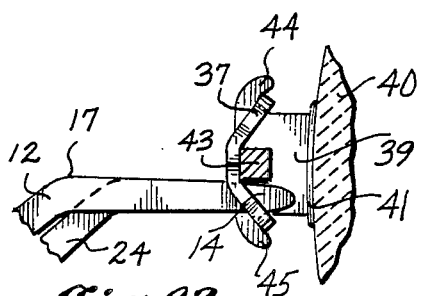
Figure 24:
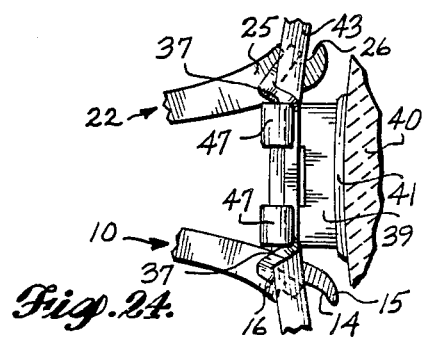

FIG. 22 is a top perspective of a portion of the manipulator head shown as executing substantially the step illustrated in FIGS. 18 and 19 in applying a ligature ring to the wings of an orthodontic bracket, FIG. 23 is a plan and FIG. 24 is an elevation of the tip portions of manipulator prongs corresponding to FIGS. 11 and 12, FIGS. 13 and 14 and FIGS. 18 and 19 illustrating still a further sequential step in applying a ligature ring to the wings of a tooth bracket,

FIG. 25 is a plan,

FIG. 26 is an elevation and

Figure 28:
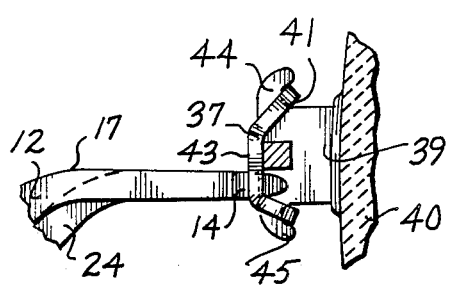
Figure 29:
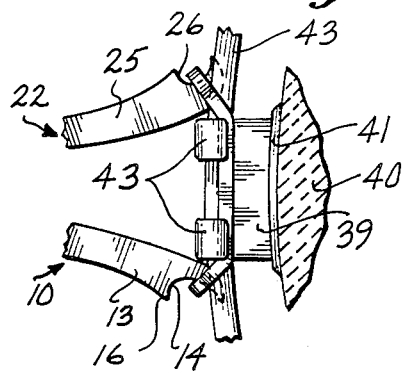
Figure 30:
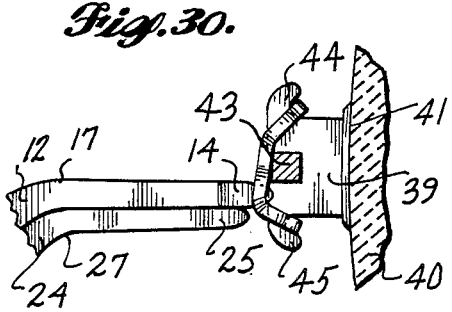
Figure 31:
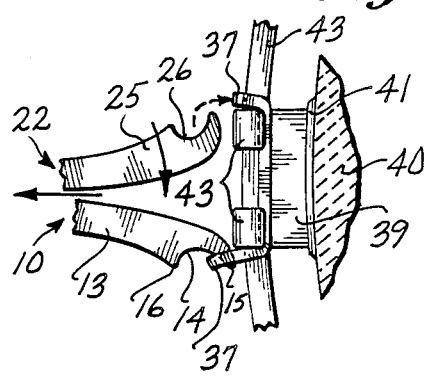
Figure 32:
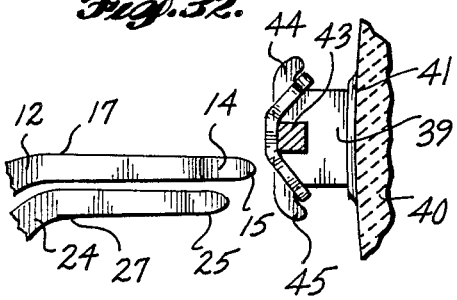
Figure 33:
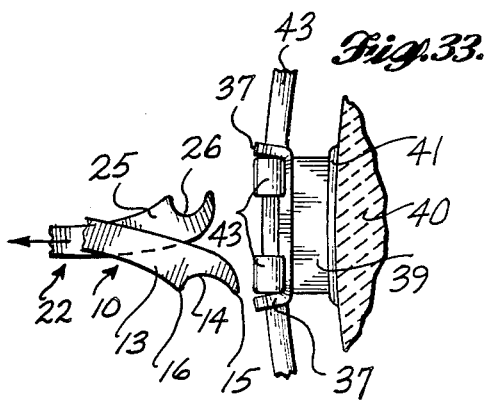
Figure 36:
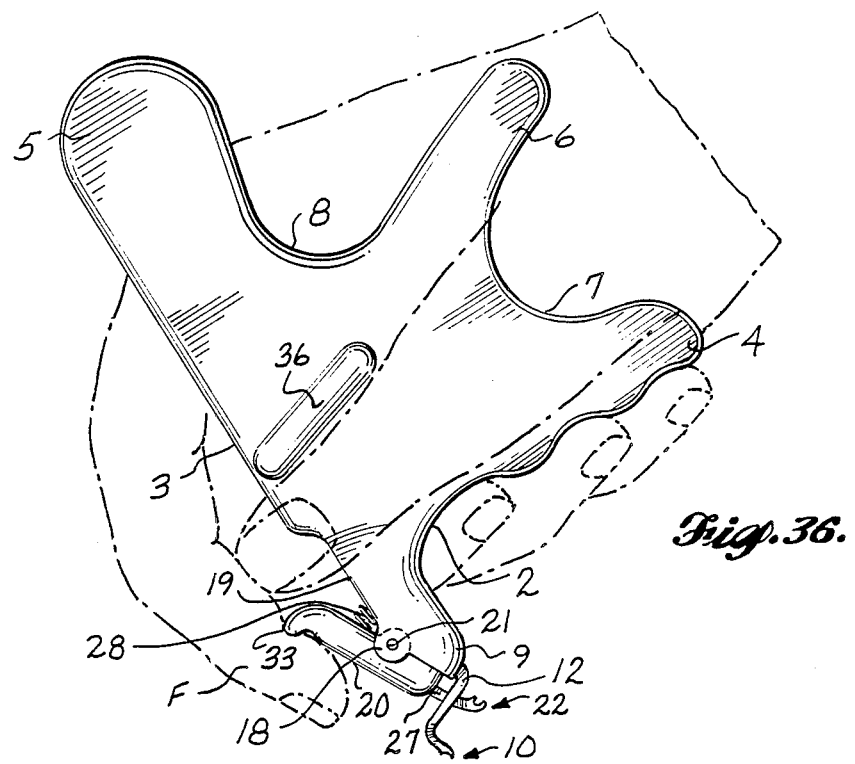
Figure 37:
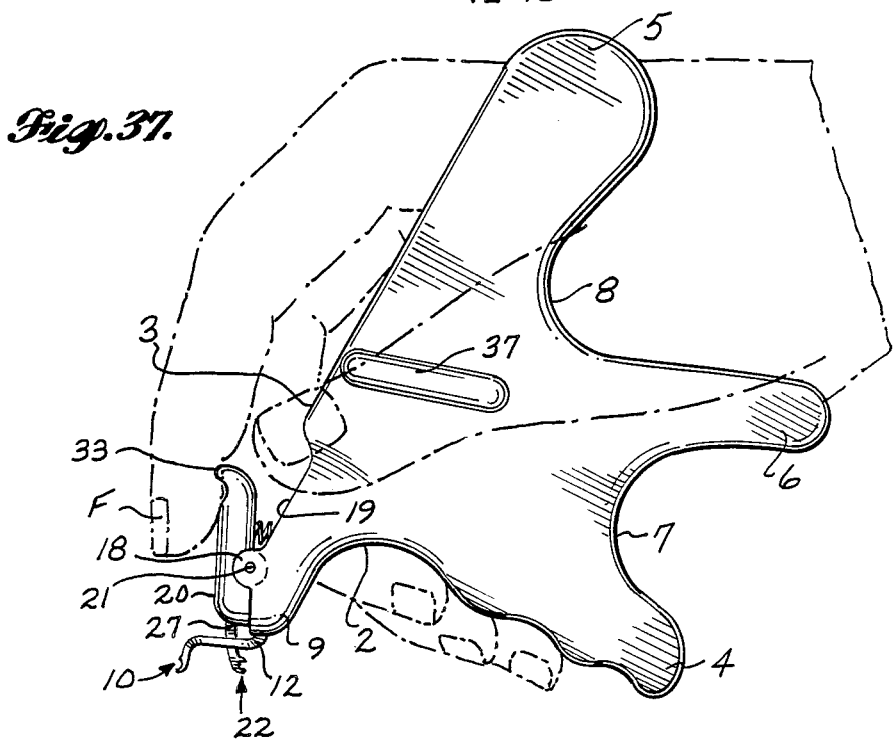
Figure 38:
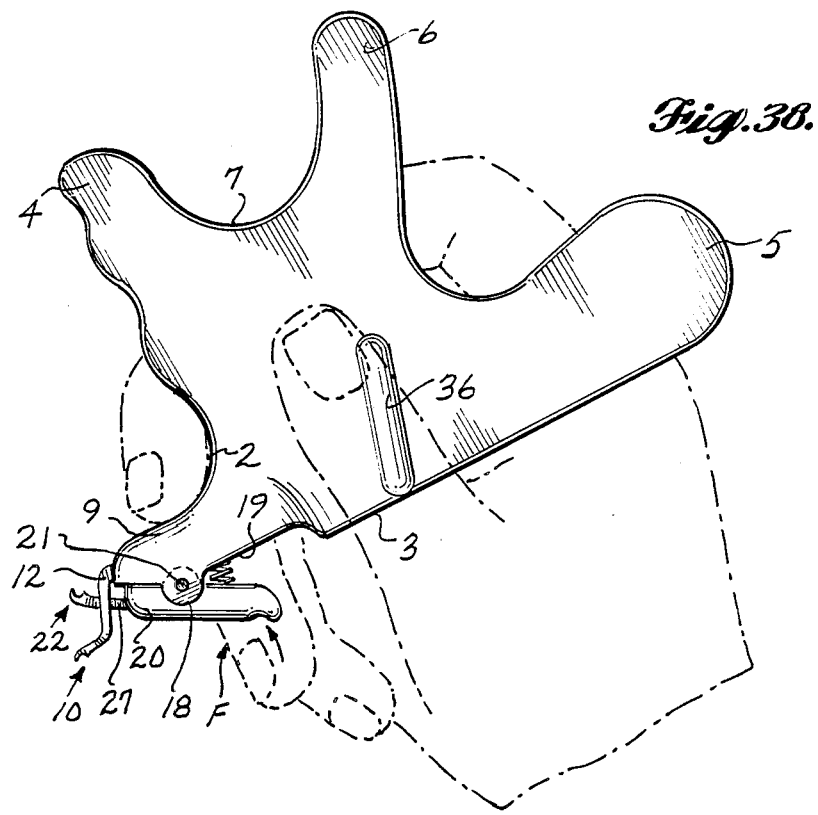
Figure 39:
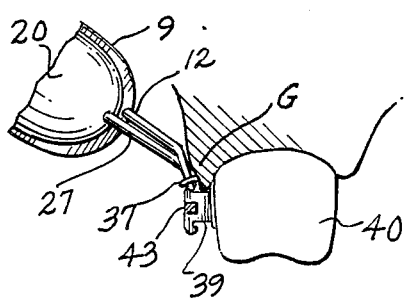
Figure 40:
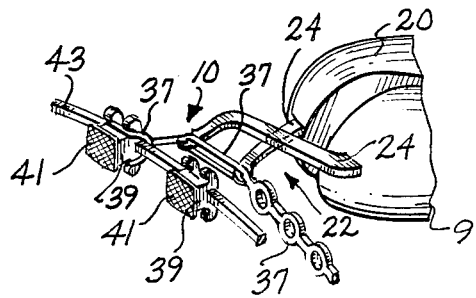
Figure 42:
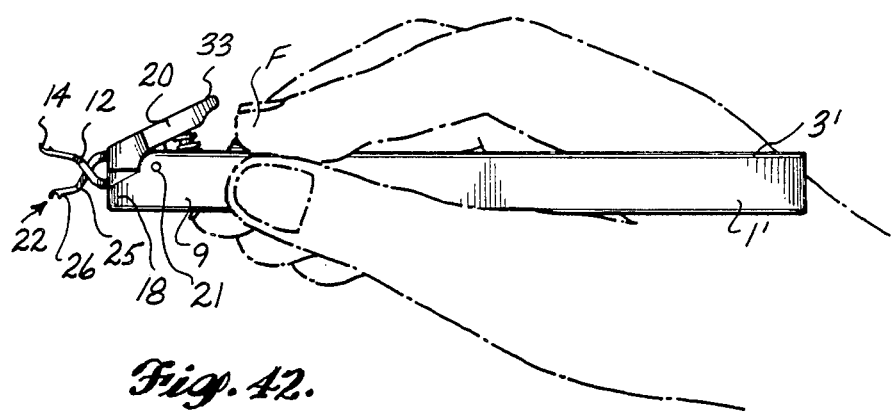
Figure 41:
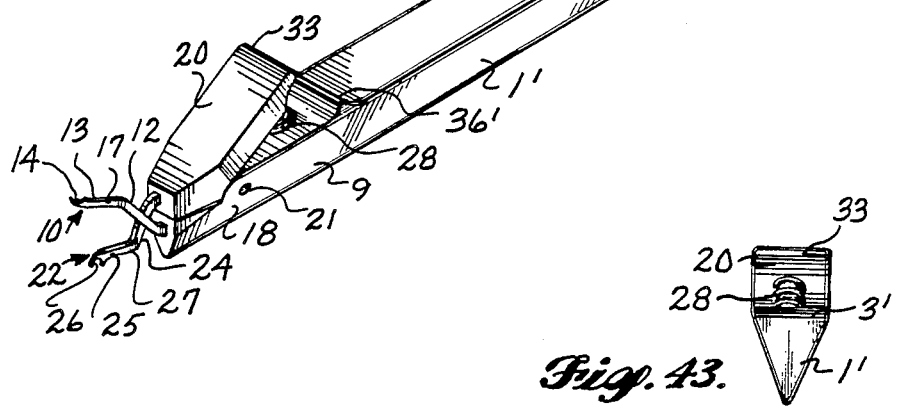
Figure 43:
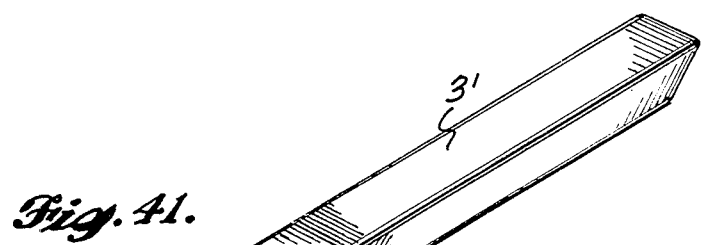
Figure 44:
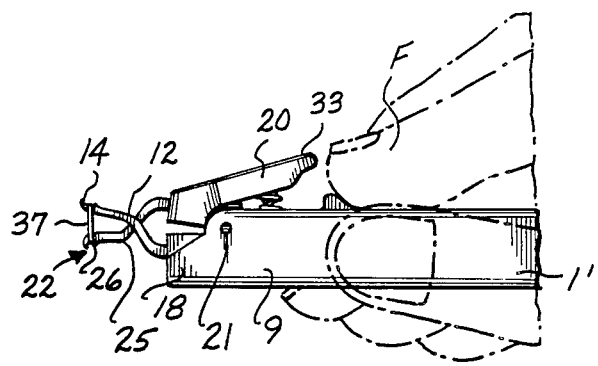
Figure 45:
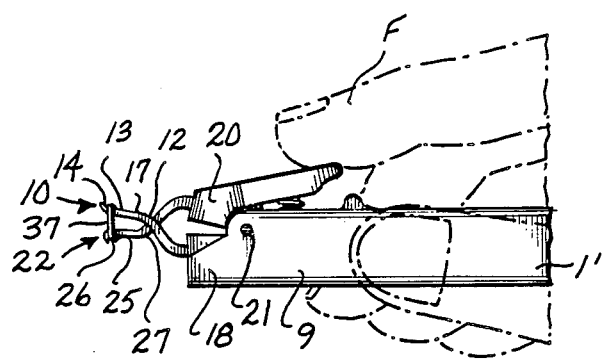
Figure 46:
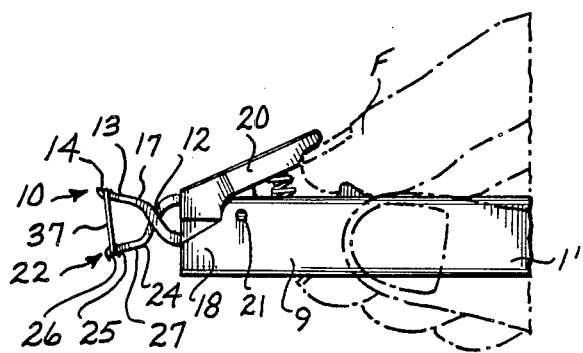

FIG. 27 is a top perspective of a portion of the head of the manipulator showing the prongs executing the step illustrated by FIGS. 23 and 24, FIG. 28 is a plan and FIG. 29 is an elevation of the top portions of prongs of the manipulator illustrating an initial step in withdrawing the prongs from a ligature ring applied to the wings of a tooth bracket, FIG. 30 is a plan and FIG. 31 is an elevation illustrating the prongs releasing the ligature ring in place on the tooth bracket wings, FIG. 32 is a plan and FIG. 33 is an elevation of the manipulator prongs immediately following full release of the ligature ring in place on the tooth bracket wings, FIG. 34 is an elevation and FIG. 35 is a top perspective of a portion of the head of the manipulator showing it in relationship to a tooth bracket corresponding to the illustration of FIGS. 32 and 33, FIG. 36 is an elevation of the manipulator illustrated as being held in one position by an operator's hand shown in phantom, FIG. 37 is a corresponding view illustrating the manipulator as being held in a different position by an operator's hand and FIG. 38 is a similar view illustrating the operator's hand as holding the manipulator in still a different position, FIG. 39 is a plan of a portion of the head of the manipulator shown with the prongs in relationship to wings of a tooth bracket attached to a tooth having overgrown gum tissue, FIG. 40 is a top perspective of a portion of the manipulator head illustrating the application of rings of an orthodontic ligature chain to the wings of tooth brackets, FIG. 41 is a top perspective of a manipulator having a modified shape of handle, FIG. 42 is a side elevation of such manipulator, and FIG. 43 is an end elevation of such manipulator, FIGS. 44, 45 and 46 are fragmentary side elevations of a portion of the manipulator of FIG. 41 showing parts in different positions, FIG. 47 is a top perspective of a third form of manipulator having prongs of different shape, FIG. 48 is a fragmentary side elevation and FIG. 49 is a fragmentary top plan of such third form of manipulator.

BEST MODE FOR CARRYING OUT THE INVENTION

Orthodontic elastomeric ligature rings require very delicate and precise manipulation in applying them to and removing them from wings of tooth brackets. The rings shown in FIGS. 6, 7 and 8 are on an enlarged scale. Typical ligature rings have an external diameter of approximately 3 millimeters and an internal diameter of approximately 1 millimeter. The wings of an orthodontic tooth bracket shown in FIGS. 11 and 12, for example, are approximately 1 millimeter in width in a direction parallel to the arch wire and are spaced apart lengthwise of the wire approximately 1 millimeter. The wings of a tooth bracket for a molar may be approximately 1½ millimeters in width and adjacent wings may be spaced apart approximately 2 millimeters so that the overall span of a pair of such wings is approximately 5 millimeters.

Because of the dimensions stated above, an applier or manipulator for orthodontic elastomeric ligature rings should be compact and must be capable of precise operation if it is to be able to pick and stretch a ring, to apply the ring to tooth bracket wings and then to be released from the applied ring reliably, easily and quickly. The manipulator of the present invention has such capabilities.

The ligature ring manipulator shown in FIGS. 1 to 5, inclusive, includes a flat or plate body 1 made of molded plastic that preferably is of trifurcated quadrant profile including two edges 2 and 3 which are generally linear and substantially mutually perpendicular and which body has three furcations between such edges. Such furcations include a furcation 4, formed partially by or located adjacent to one generally linear edge 2 of the body, a second furcation 5 formed by or located adjacent to the other generally linear edge 3 of the body and a third furcation 6 projecting radially from the body substantially midway between the furcations 4 and 5. A crotch or throat 7 is formed between the adjacent furcations 4 and 6 and a crotch or throat 8 is formed between the furcations 5 and 6. Such body is adapted to be held clamped between a user's thumb engaging one body face and a user's first and second fingers engaging the opposite face of the body.

The manipulator includes a head 9, which may be made of molded plastic, integral with and projecting from the apex of the quadrant body generally in prolongation of edge 3 of the body as shown in FIGS. 1 and 2, the length of the head extending transversely of the other edge 2 of the body as shown in FIG. 2. Such head carries prongs which can be used to pick and stretch a ring and hold the ring in such stretched condition automatically while the manipulator is being manipulated to apply the ring to the wings of a tooth bracket. Such prongs include a fixed prong 10 shown best in FIG. 2 as having an anchored end portion 11 embedded in the projecting end of the head 9, a shank 12 bent relative to the length of the head and projecting away from the body and a tip portion 13 bent transversely of the shank 12 at an angle of 90 degrees to 115 degrees, preferably about 105 degrees.

The tip portion of the fixed prong, which is offset from its embedded end portion 11 by the shank 12, has in it a shallow notch 14 adjacent to the tip 15 which notch opens away from the body. Such notch forms the tip 15 as a probe which is substantially pointed and further forms a shoulder 16 at the side of the notch opposite the tip 15. The tip portion 13 of the probe is canted relative to the shank at an angle of 20 to 60 degrees, preferably approximately 40 degrees, relative to the plane of the body 1 by a bend 17, as shown best in FIG. 5.

From the opposite sides of the head 9, ears 18 spaced transversely of the body project beyond the edge of the head remote from the body to form a recess 19 between them for receiving a rocker or lever 20. Such rocker is secured in such recess by a pivot 21 extending between the ears 18 through a transverse bore in the rocker located generally centrally between its ends.

From the end of the rocker 20 remote from the body 1 projects a prong 22 movable with the rocker and having an anchored end portion 23 embedded in the end of the rocker remote from the body 1, so that the rocker constitutes a mounting member for the movable prong. A shank 24 of the prong projects from such anchored end portion into substantially mutually perpendicular crossing relationship with the shank 12 of fixed prong 10. The pivot 21 is located approximately midway between the tip 25 of prong 22 and the end of rocker 20 remote from such prong, as shown in FIGS. 2 and 3. In the tip portion 25 of movable prong 22 is a notch 26 opening away from the tip portion 13 of prong 10. Such notch is adjacent to the tip of prong 22 and is deeper and narrower than the notch 14 in the tip 13 of prong 10. The tip portion 25 of movable prong 22 is canted relative to its shank 24 and the central plane of body 1 by a bend 27 through an angle of 20 degrees to 60 degrees, preferably approximately 40 degrees, so that the tip portion of the two prongs are in substantially parallel planes, as shown in FIG. 5.

The crossing relationship of the shank 12 of fixed prong 10 and the shank 24 of movable prong 22 can be changed from a substantially mutually perpendicular crossing relationship preferably even into the uncrossed position shown in FIG. 3 by tilting rocker 20 about its pivot 21 relative to head 9 and body 1. The rocker is urged toward its limiting position shown in FIG. 2 by a spring which may be a helical compression spring 28 having one end seated in a socket 29 in the bottom of recess 19 and its other end seated in a socket 30 in the end portion 31 of the rocker 20 at the side of pivot 21 remote from prong 22. Since the notch 26 forms a hook engageable with a ligature ring, constituting a load, and it is at the side of pivot 21 remote from spring 28 applying a force to the rocker 20, such rocker constitutes a lever of the first class.

The underside of the portion 31 of rocker 20 at the side of pivot 21 adjacent to the body makes an angle of 20 degrees to 40 degrees, preferably about 30 degrees, to the bottom of the recess 19 so that the rocker can rock relative to the head 9 and body 1. The edge of the head facing the rocker is crowned with a ridge adjacent to the pivot 21 so that the portions of such edge at opposite sides of the pivot form an included angle of 140 degrees to 160 degrees, preferably approximately 150 degrees, so as to enable the rocker to rock relative to the head for changing the relationship of movable prong 22 relative to fixed prong 10.

Spring 28 urges the rocker toward the limiting position shown in FIG. 2, but it can be rocked into its other limiting position shown in FIG. 3 by the tip of a finger F of the operator pressing on the end portion 31 of the lever. The tip of lever portion 31 preferably has an upswept crest 33 providing a surface 34 against which pressure can be exerted by the tip of the forefinger to press the end portion 31 of the lever away from the edge 19 of the head if desired. Also, a thumb-receiving recess 35 is the side of the body and an adjacent thumb-engageable rib 36 on the side of the body may be provided, if desired.

FIGS. 6, 7 and 8 illustrate a procedure for using the manipulator to pick a ligature ring 37 off a spindle 38. Such rings may be disconnected or may be connected by a thin strand. The first step is for the hook formed by notch 26 of the movable prong 22 to hook one portion of the ring loop as shown in FIG. 6. The manipulator is then pulled away from the spindle 38 in the direction indicated by the arrow in FIG. 6 to stretch the ring until the manipulator can be inclined to the position shown in FIG. 7. The force exerted on the movable prong by the ring as the manipulator is thus pulled and inclined will tilt the rocker 20 relative to the head 9 to the position shown in FIG. 7 in opposition to the force exerted by spring 28. With the rocker in that position, the probe tip 15 of prong 10 can be poked into the slot to which the aperture of the ring is deformed, as shown in FIG. 7. The notch 14 of prong 10 can then engage the side of the uppermost ring loop generally opposite the portion of such ring loop engaged by the notch 26 of prong 22.

When the ring is held between the notches 26 and 14 of the prongs 22 and 10 in stretched condition, the manipulator can be lifted from the position shown in FIG. 7 to the position of FIG. 8 to withdraw the uppermost ring easily from the spindle 38, breaking any strand connecting adjacent rings. The notch 26 of prong 22 is not deep enough to engage the next lower ring and, when the uppermost ring is stretched, the probe tip 15 can easily be inserted between the uppermost ring and the next lower ring without disturbing such next lower ring.

The spring 28 is designed so that the rocker 20 will assume an attitude of equilibrium relative to the head 9 substantially in the position shown in FIG. 9 when a ligature ring has been picked and is being held by the prongs as shown in that figure. In such an attitude of rocker 20, the force exerted by spring 28 multiplied by the distance between the spring and the rocker pivot 21 will produce a moment equal to the moment produced by the force exerted by the stretched ring 37 multiplied by the distance between notch 26 gripping such ring and the pivot 21. The force produced by compressed spring 28 should be related to the resistance to stretching of ring 37 with respect to the lever arms of such forces such that the spacing of the prong tips 13 and 25 will be slightly greater than 3 millimeters, which is the approximate composite width of the wings and spacing of a tooth bracket. The rocker will be maintained in the attitude relative to head 9 shown in FIG. 9 automatically without the application of finger pressure to the rocker.

If the ligature ring is to be applied to a tooth bracket having a greater composite width of the wings and spacing, such as a molar tooth bracket, the operator may press his finger against the end surface 34 of the rocker crest 33 to assist the spring 28 in rocking the rocker 20 farther to increase the spacing between the tips 13 and 25 of the prongs as shown in FIG. 10. If the pressure of the finger on the surface 34 is removed, the tension of the ligature ring will not draw the movable hook 26 toward the fixed hook 14 again to the positions shown in FIG. 9, because the additional stretching of the ring will subject the material to some permanent deformation. If the ring is somewhat overstretched, therefore, the new force equilibrium position of the prongs without further application of finger pressure to the rocker will be such that their spacing will be maintained automatically slightly greater than the spacing required to place the ring on the wings of a molar tooth bracket, such as slightly in excess of 5 millimeters. Alternatively the rocker end 31 may be pressed with the finger to reduce the force of spring 28 on the rocker to some extent to reduce the stretch of the ring. Thus the prongs can be adjusted so as to vary infinitely the degree of stretch of the ring between the limits of tilt of the rocker 20.

A tooth bracket, which is not a molar tooth bracket, to which it is desired to apply a ligature ring is shown in FIGS. 11 to 35. The base of the tooth bracket 39 is bonded to the face of the tooth 40 by a layer of adhesive 41. The bracket is applied to the tooth so that the length of the groove 42 in its outer face extends circumferentially of the tooth arch to receive in it an arch wire 43. The bracket has a pair of wings 44 at one side of the groove 42 and a pair of wings 45 at the other side of such groove which the ligature ring can encircle spanning the groove 42 to hold the arch wire 43 in the groove.

Figure 11:
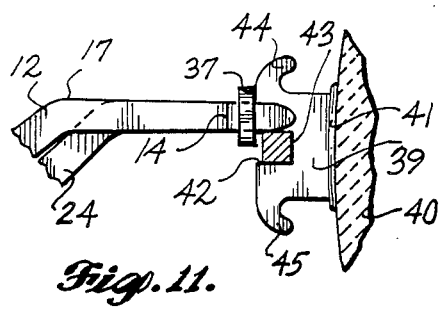
Figure 12:
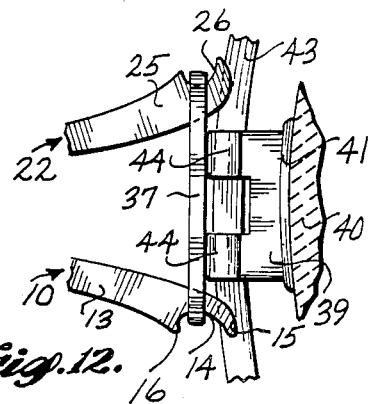
Figure 13:
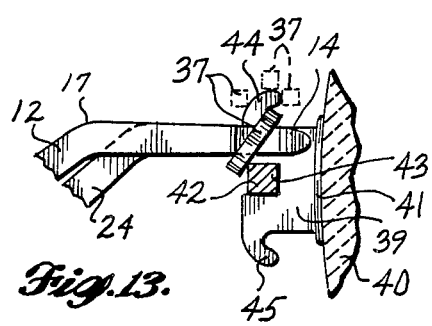
Figure 14:
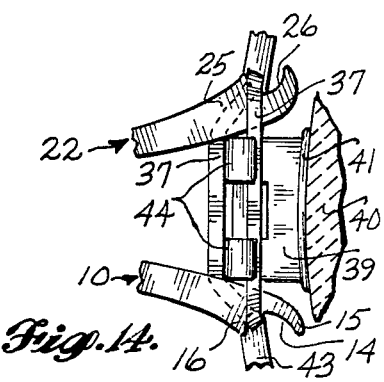

After a ligature ring has been picked from a ring supply, such as is the manner illustrated and described in connection with FIGS. 6, 7, 8 and 9, the tips of the manipulator prongs can be placed against the arch wire with the stretched ring straddling the tooth bracket 39, as shown in FIGS. 11 and 12. Without appreciably changing the tilt of the prongs relative to the bracket, the manipulator can then simply be pushed toward the tooth so that the shoulders of the notches remote from the prong tips will push one stretch of the ring against the wings 44 to be wedged away from the prongs 10 and 22 by engagement with the curved outer sides of the adjacent wings 44, as shown in broken lines in FIG. 13, so that such stretch of the ring will slide away from the groove 42 over the tips of those wings and snap in behind the curved wings, as shown in FIGS. 13 and 14. If the ring is not stretched quite enough, pressure of the divergent prongs on the bracket wings will spread the prongs automatically, as shown in FIG. 14, enough to enable the ring stretch to slide over the bracket wings.

Next, the manipulator is pulled slightly away from the tooth, shifted to the opposite side of the arch wire 43 by the motion illustrated by broken lines in the upper portion of FIG. 18 and in FIGS. 20 and 21, to the position shown in solid lines in FIGS. 18 and 19, and again is pushed toward the tooth at such opposite side of the arch wire, as indicated in the lower broken lines in FIG. 18. Such movement will wedge the other stretch of the ligature ring to slide over the tips of the wings 45, as indicated in broken lines in FIG. 18, until it snaps behind the curved wings 45. The ligature ring will then be in place encircling all the wings 44 and 45 and holding the arch wire 43 securely in the bracket groove 42.

The tension of the ring opposing the stress of spring 28 will hold the prongs from spreading more than necessary as the ring is thus shifted and will even draw the prongs toward each other to maintain them in contact with the bracket as the manipulator is pulled back and the ring is stretched so as to minimize stretching of the ring.

As has been mentioned in describing the procedure for applying the ligature ring to the wings of a tooth bracket in connection with FIGS. 11 to 14, 18, 19, 23 and 24, it is usually not necessary to tilt the manipulator appreciably in applying a ring to a tooth bracket, but the manipulator is simply moved toward and away from the tooth. The position of the manipulator during the application of the first stretch of ligature ring 37 to the tooth bracket wings 44 is illustrated in FIGS. 15, 16 and 17. It will be noted in FIG. 15 that, because of the cant of the tip portions of the prongs relative to their shanks, the plane of the body of the manipulator can be inclined downward at an angle of 20 to 40 degrees relative to the plane of the tooth arch during the procedure of applying a ligature ring to a tooth bracket by the procedure described so that the hand of the operator and the manipulator will not obscure the line of vision of the operator to the ligature ring and the tooth bracket. Because the angle of tilt of the manipulator need not be changed appreciably, if at all, during most procedures for applying a ligature ring to the wings of a tooth bracket, as indicated by FIGS. 15, 20 and 25, the line of vision of the operator remains unobstructed during the entire operation of applying a ligature ring to the wings of a tooth bracket.

In describing the prongs of the manipulator in connection with FIG. 2, it was noted that the movable prong 22 was shorter than the fixed prong 10 so that a line connecting their tips was disposed at an angle of 10 to 30 degrees, preferably about 20 degrees, relative to the edge 2 of the quadrant body 1 or at an angle of 60 degrees to 80 degrees, preferably 70 degrees, to the edge 2 of the body 1. This angle may increase slightly relative to edge 2 and correspondingly decrease slightly relative to edge 1 as the rocker 20 is rocked to move the tip portion 25 of the prong 22 toward the tip portion 13 of prong 10. Such angular relationship will determine the attitude of the body 1 relative to the tooth arch when a ligature ring is being placed on the wings of a tooth bracket because, as shown best in FIGS. 16, 21 and 26, the manipulator is held with the line joining the prong tips disposed substantially parallel to a tangent to the curved arch wire and tooth arch at the location of the tooth bracket to which the ligature ring is being applied. Consequently, during such ring application, the body 1 of the manipulator will be held relative to the arch wire and tooth arch, as indicated in FIG. 21, with the edge 2 of the manipulator quadrant at an angle of 10 to 30 degrees to the tangent to the arch wire, which will result in side 3 being generally perpendicular to such tangent, and the tooth arch at the location of the tooth bracket to which the ligature ring is being applied. Thus, the attitude of the manipulator body during such applying operation will be governed by the angular relationship between the tips of the prongs and the edge 2 of the manipulator body. Such angular relationship enables the manipulator to be held more conveniently by the operator, enables the body of the manipulator and the hand holding it to be more easily positioned out of the line of vision of the operator to the ligature ring and retracts the cheek to facilitate access. The offset of the fixed prong also contributes to the convenience with which the manipulator can be held, to keeping it out of the line of vision of the operator and assisting in retracting the cheek.

When the application of the ring to the wings of a tooth bracket has been completed, as shown in FIGS. 23 to 27, it is then necesssary to release the hooks 14 and 26 of the manipulator from the applied ring. The sequence of steps to effect releasing of the manipulator hooks from the ring is illustrated in FIGS. 28 to 35. The hooks of the manipulator prongs can be removed from the ligature ring placed on the orthodontic bracket without appreciably changing the attitude of the body relative to the arch wire and tooth arch, as will be evident particularly from a comparison of the body positions shown in FIGS. 21 and 34.

Moreover, the hooks of the manipulator prongs can be released from a ligature ring after it has been applied to a tooth bracket merely by tilting the rocker 20 relative to the body by applying pressure with the forefinger to the crest 33 of the rocker in the manner illustrated in FIGS. 3 and 34. By such pressure, the rocker will be tiled from its position shown in FIGS. 16, 21 and 26 to the position of FIG. 34.

The sequence of movements of the prong hooks relative to the ligature ring as such hooks are withdrawn from the ring begins with the step illustrated by FIGS. 28 and 29 in which the manipulator is simply pulled slightly away from the tooth after the final step of applying the ring illustrated by FIGS. 23 and 24. As the prongs are then moved toward each other by finger pressure on the crest 33 of the rocker 20 to tilt the rocker for moving movable prong tip 25 toward stationary prong tip 13, such tips may engage opposite sides of the bracket wings and by pressure on such sides actually wedge the tips away from the bracket. As the rocker 20 is rocked farther the deep notch 26 of the shorter movable prong 22 is withdrawn from the ligature ring by movement of the prong tip generally parallel to the arch wire 43, as shown in FIGS. 30 and 31. When the tips of prongs 22 and 10 are in this relationship relative to the applied ligature ring, farther withdrawal of the manipulator in the direction indicated by the arrow in FIG. 31, away from the arch wire and bracket, will pull the probe 15 of the fixed prong out of the other side of the ligature ring, as shown in FIGS. 32 and 33.

It can be seen from FIG. 31 that it is not necessary to tilt the rocker 20 relative to the body to the point where the tip portion 25 of the movable prong overlaps the tip portion 13 of the fixed prong in order to withdraw the manipulator hooks from the ligature ring which has been applied to the wings of a tooth bracket, but it is easier for the operator simply to tilt the rocker substantially fully relative to the manipulator body so that the tip portions 25 and 13 of the prongs pass each other as shown in FIGS. 3, 34 and 35. Such uncrossing of the prongs is particularly beneficial to facilitate release of the prong tips from the ligature ring where the bracket is very narrow, such as a single bracket.

As has been explained in connection with FIGS. 21 and 26, a line joining the tips of movable prong 22 and fixed prong 10 during the application of a ligature ring to the wings of a tooth bracket is substantially parallel to a tangent to the arch wire arch and to the tooth arch at the location of the tooth bracket to which the ring is being applied. Consequently, the attitude of the manipulator relative to the tooth arch must be changed as the ligature rings are applied to the brackets on different teeth. Both the angle between a line joining the tips of the prongs and the edge 2 of the manipulator body and the provision of different furcations on the body contributes to the convenience of holding the body for applying ligatures to the bracket bonded to different teeth. Normally, a right-handed operator sits to the right, and at times somewhat behind, a reclining patient to whose tooth brackets an arch wire is being secured. To reduce the reach required by an operator to apply ligature rings to the tooth brackets in the left side of the patient's mouth, the web of the operator's hand between the thumb and forefinger can be fitted into the throat or crotch 7 between the furcations 4 and 6 as illustrated in FIG. 36.

When the manipulator is being used to apply ligature rings to brackets on the front teeth, the operator's grip can be shifted so that the web between his thumb and forefinger is fitted into the crotch or throat 8 between the furcations 5 and 6, as shown in FIG. 37.

When the operator is applying ligature rings to brackets on teeth in the right side of the patient's mouth, the manipulator can be inverted side-for-side and grasped between the thumb and forefinger as shown in FIG. 38. When the manipulator is held in this position, the tip of the second finger can be used to press on the crest 33 of the rocker 20 as necessary to stretch the ring or to release the manipulator prong notches from the applied ring.

Usually, there is ample clearance between a tooth bracket and the gum of the tooth to which it is attached, as shown in FIGS. 15, 20 and 25. In some instances, however, the gum tissue is swollen or the tooth is deeply embedded in the gum so that a tooth bracket must be bonded to the tooth close to the overhanging or overgrown gum as shown in FIG. 39 in order for its arch wire slot to be substantially in the plane of the remainder of the arch wire arc. In such instances, the cant of the prong tip portions 25 and 13 relative to the shanks 24 and 12 of their respective prongs facilitates insertion of the prong tips between the gum G and the gingival wing of the tooth bracket, as illustrated in FIG. 39.

While the foregoing description has described the application of single ligature rings to the wings of tooth brackets, the manipulator can also be used conveniently to apply to tooth brackets the rings of twin rings connected by a tie, or multiple rings connected by ties to form a chain, as shown in FIG. 40. Such interconnected rings can be applied, respectively, to successively adjacent tooth brackets around a tooth arch, or successive rings can be applied to tooth brackets which are spaced from each other by one or more intermediate brackets. In any of such instances, any of such interconnected rings can be distended individually and applied to the wings of a selected tooth bracket, as indicated in FIG. 40, in the same manner as described above as being utilized in applying individual ligature rings to tooth brackets.

In addition, the probe end 15 of such fixed prong 10 may be used as a ligature director and can also be used to pick ligature rings off the wings of a tooth bracket when it is desired to remove such rings.

In the manipulator shown in FIGS. 41 to 46, inclusive, the body of the manipulator adapted to be held clamped between a user's thumb and the first and second fingers is of rod shape instead of being a flat or plate body. Such rod is preferably of isosceles triangular cross section, as shown best in FIG. 43. The body 1' has a head 9 at one end including ears 18 spaced transversely of the body to form a recess between them for receiving the rocker 20. Such rocker is similar to the rocker of the manipulator described in connection with FIGS. 1 to 4.

The rocker 20 received between the ears 18 of the head 19 is pivoted by pivot 21 extending between the ears through a transverse bore in the rocker located generally centrally between its ends for guiding the rocker for rocking relative to the manipulator head.

From the end of the rocker 20 remote from the body 1 projects a prong 22 and from the adjacent end of the head projects a fixed prong 10 shaped and arranged like the prongs carried by the rocker and body head described in connection with FIGS. 1 to 4. These prongs are used to hold a ligature ring, as shown in FIGS. 44, 45 and 46 for application to the wings 44 and 45 of a tooth bracket 39, as described in connection with FIGS. 9 to 35. In this connection, the end portion of the body 1' adjacent to the head 9 has a cross-rib 36' shown in FIG. 47 against which the first finger of the hand can press, as shown in FIGS. 44 and 46.

The type of manipulator shown in FIGS. 47, 48 and 49 is similar to the manipulator described in connection with FIGS. 41 to 46, inclusive, except for the shape of the prongs projecting from the head 2 and the adjacent end of head 20 in cooperating relationship. This manipulator includes a fixed prong 50 projecting from the head end 9 of the body 1' and a cooperating movable prong 51 projecting from the adjacent end of the rocker 20 which is carried by the head of the body.

In the manipulators described in connection with FIGS. 1 to 46, the ring-gripping prongs are disposed generally in a plane perpendicular to the axis of the rocker pivot 21. In the manipulator shown in FIGS. 47 to 49, on the contrary, while the prongs 50 and 51 can be moved relatively generally in the same manner as the prongs of the manipulators shown in FIGS. 1 to 46, the prongs, themselves, are disposed generally in planes parallel to the axis of pivot 21 rather than being perpendicular to such axis.

The fixed prong 50 includes an offset shank 52 projecting in cantilever fashion from the central portion of the end of the manipulator head 9. The end of such shank carries divaricated outcurved, oppositely extending prong elements 53. The end of each prong element has a hook 54 opening away from the movable prong 51 when the rocker 2 is in its limiting position engaged with the head 9, as shown in FIG. 48. The rong portions 53 are curved outward away from each other and from the end of shank 52 backward toward the body 1'.

The movable prong means 51 carried in cantilever fashion by the rocker 20 includes two prong shanks 55 straddling the fixed shank 52. The prong shanks 55 are offset away from the fixed prong members 53 so that the prong members 56 carried by shanks 55 are spaced farther from the prong members 53 than they would otherwise be.

The movable prong members 56 carried by the prong shanks 55 are outcurved away from each other and back toward the manipulator body 1', as shown best in FIG. 49. The tips of the prong members 56 have hooks 57 opening away from the fixed prong members 53. The lengths of the fixed prong members 53 and of the movable prong members 56 are generally equal so that the hooks 54 of the stationary prong members and the hooks 57 of the movable prong members are in substantially overlying relationship as shown in FIG. 49. The shanks 55 of the movable prong members preferably are somewhat shorter than the shank 52 of the fixed prong members so that the hooks 57 of the movable prong members are located closer to the manipulator head 9 than are the hooks 54 of the fixed prong members, as shown best in FIG. 48.

The manipulator shown in FIGS. 47 to 49 can be operated to apply ligature rings to the wings 45 of the tooth bracket 39 in generally the manner described in connection with FIGS. 11 to 35, but the type of manipulator shown in FIGS. 47 to 49 is especially designed to be used for applying ligature rings to and removing such rings from the wings of tooth brackets applied to the lingual faces of teeth. The manipulator of FIGS. 47 to 49 has two sets of hooks to facilitate manipulating ligature rings on the left side and on the right side of the teeth arches, respectively.

What is claimed is:

1. An orthodontic elastomeric ligature ring manipulator comprising an elongated body including a handle adapted to be grasped between the thumb and at least one finger of a hand, a first prong having its root fixed to a portion of said body spaced from said handle and said first prong projecting from its root beyond said body, a lever less than half the length of said handle, pivot means mounting said lever on said body and located generally centrally between the ends of said lever and between said first prong and said handle, and a second prong carried adjacent to said first prong by one end portion of said lever remote from said handle for movement relative to said first prong by rocking of said lever relative to said body, and the other end portion of said lever closer to said handle being engageable by the tip of a finger of the hand grasping said handle to rock said lever relative to said body, said prongs having tips with hooks opening away from each other for holding an elastomeric ring stretched between said hooks.

2. The manipulator defined in claim 1, in which the hooks are formed by notches in the tips of the prongs and the notch in the second prong tip is deeper than the notch in the first prong tip.

3. The manipulator defined in claim 2, in which the notch in the first prong tip is sufficiently close to the tip end of the first prong and is sufficiently shallow that the tip of the first prong forms a probe extending lengthwise of such prong.

4. The manipulator defined in claim 1, in which one of the prongs is shorter than the other prong.

5. The manipulator defined in claim 4, in which the tip of the shorter prong is closer than the tip of the other prong to the body.

6. The manipulator defined in claim 1, in which the body is of rod shape.

7. The manipulator defined in claim 6, in which the body is of triangular cross section.

8. The manipulator defined in claim 1, in which at least one of the prongs is disposed generally in a plane parallel to the rocker axis.

9. The manipulator defined in claim 1, in which at least one of the prongs has a shank portion and a tip portion, said tip portion including divaricated, outcurved, oppositely extending prong elements.

10. The manipulator defined in claim 1, in which a first one of the prongs includes two substantially parallel shanks and tip portions outcurved respectively from said shanks.

11. The manipulator defined in claim 10, in which the outcurved prong tip portions are curved respectively back toward the body portion.

12. The manipulator defined in claim 10, in which the other prong includes a shank extending between the two shanks of the first prong.

13. The manipulator defined in claim 1, in which the end of the lever remote from the second prong is formed as an upswept crest engageable by a finger of the hand grasping the body.

14. In the manipulator defined in claim 1, the body having spaced ears projecting from one side thereof away from the body for receiving the lever between them and clearance being provided between the lever and the body to enable the lever to rock relative to the body.

15. In the manipulator defined in claim 1, spring means urging the lever to rock relative to the body in the direction to move the prongs apart.

16. In the manipulator defined in claim 1, a helical compression spring engaged between the body and the lever for urging the lever to rock in the direction to move the tip of the second prong away from the tip of the first prong.

17. In the manipulator defined in claim 16, the lever being formed as a rocker and the end of the rocker engageable by the tip of a finger of the hand grasping the handle being formed as an upswept crest.

18. In the manipulator defined in claim 17, the rocker being pivotally mounted on the body to rock about a pivot axis approximately midway between the tip of the second prong and the end of the rocker remote from the second prong.

19. In the manipulator defined in claim 1, the handle being of substantially flat trifurcated shape and the body having a head projecting therefrom in the direction generally opposite one furcation of the handle, the first prong projecting from the end of said head away from the handle.

20. In the manipulator defined in claim 19, the lever being formed as a rocker with its pivot mounted on the head, said rocker being of a length approximately equal to the length of the head.

21. The manipulator defined in claim 20, in which the rocker is pivotally mounted to rock about a pivot axis approximately midway between the tip of the second prong and the end of the rocker remote from the second prong.

22. The manipulator defined in claim 21, and a helical compression spring engaged between the portion of the rocker at the side of the pivot axis remote from the second prong for urging the rocker to rock in the direction to move the tip of the second prong away from the tip of the first prong.

23. In the manipulator defined in claim 19, two of the body furcations forming body edge furcations and the third body furcation being located substantially midway between said body edge furcations.

24. In the manipulator defined in claim 23, the included angles between the third body furcation and the two edge body furcations being approximately equal.

25. The manipulator defined in claim 1, in which the tip of the first prong is offset from its root a substantial distance.

26. The manipulator defined in claim 1, in which the first prong includes an elongated tip portion, a shank disposed at an angle to said tip portion of the first prong for offsetting the tip of the first prong a substantial distance from its root, and the second prong includes a shank crossing said shank of the first prong at a location spaced from the axis of the pivot means.

27. The manipulator defined in claim 1, and spring means urging the lever to rock for moving the second prong away from the first prong toward a limiting position, the elastomeric ring extending between the hooks exerting a force opposite the force exerted by said spring means sufficient to hold the second prong closer to the first prong than the distance between such second prong limiting position and the first prong.

28. The manipulator defined in claim 1, in which each prong has a shank portion and a tip portion, said shank portions being disposed in substantially parallel planes and said tip portions being canted, respectively, at an angle relative to the respective planes of said shank portions of the prongs.

29. The manipulator defined in claim 28, in which the prong tip portions are canted approximately equally relative to the respective shank portions of the prongs so that the tip portions of the two prongs are in substantially parallel planes intersecting the planes of the shank portions of the prongs.

30. An orthodontic elastomeric ligature ring manipulator comprising a substantially flat trifurcated body adapted to be grasped between the thumb and at least one finger of a hand and having a head projecting therefrom in the direction generally opposite one furcation of said body, a first prong projecting from the end of said head away from said body, and a second prong carried by said body adjacent to said first prong, said prongs having tips with hooks opening away from each other for engagement with an elastomeric ring extending between said hooks.

31. The manipulator defined in claim 30, in which two of the body furcations form edges of the body, respectively, and the third body furcation is substantially midway between said edge furcations.

32. The manipulator defined in claim 31, in which the included angles between the third body furcation and the two edge body furcations are approximately equal.

33. An orthodontic elastomeric ligature ring manipulator comprising a body having two prongs projecting therefrom in adjacent relationship, said prongs having shank portions and having tip portions projecting from said shank portions with hooks opening away from each other for holding an elastomeric ring extending between said hooks, said tip portion of one of said prongs being bent relative to said shank portion of such prongs and said shank portion and said tip portion of the other of said prongs being generally in alignment to dispose said shank portions generally perpendicular to each other and said tip portions generally parallel to each other.

34. The manipulator defined in claim 33, in which the shank portions of the two prongs are disposed in crossed relationship.

35. An orthodontic elastomeric ligature ring manipulator comprising a body having two prongs projecting therefrom in adjacent relationship, said prongs having tips with hooks opening away from each other for holding an elastomeric ring extending between said hooks, one of said prongs being considerably shorter than the other of said prongs.

36. An orthodontic elastomeric ligature ring manipulator comprising a body having two prongs projecting therefrom in adjacent relationship, said prongs having tips with hooks opening away from each other for holding an elastomeric ring extending between said hooks, pivot means guiding said prongs for relative movement, and one of said prongs including a shank portion and a tip portion bent relative to said shank portion in a direction toward the other prong.

37. An orthodontic elastomeric ligature ring manipulator comprising a body having two prongs projecting therefrom in adjacent relationship, said prongs having tips with notches opening away from each other for holding an elastomeric ring extending between said notches, one of said notches being shallower than the other of said notches and shaping the tip portion of its prong as a probe extending lengthwise of such prong.

38. An elastomeric ligature ring manipulator comprising a body having two prongs projecting therefrom in adjacent relationship, said prongs having tips with hooks opening away from each other for holding an elastomeric ring extending between said hooks, and pivot means mounting said prongs for relative movement to vary the spacing between said prong tips, said prongs including shank portions between said pivot means and said prong tips, and said pivot means guiding said prongs for relative movement between a position in which said prong shank portions are uncrossed and a position in which said prong shank portions are crossed approximately perpendicularly at a location spaced from the axis of said pivot means.

39. The manipulator defined in claim 38, and spring means urging the prongs to move relatively into a relationship in which the prong shank portions are crossed.

40. An orthodontic elastomeric ligature ring manipulator comprising a body adapted to be grasped between the thumb and at least one finger of a hand, a first prong projecting from said body and having its root fixed relative to said body, said first prong including an elongated tip portion and a generally straight shank disposed at an angle to and carrying said tip portion for offsetting said tip portion a substantial distance from its root, and a second prong adjacent to said first prong, supported from said body for movement relative to said first prong and including a generally straight shank crossing said shank of said first prong substantially perpendicularly, said prongs having tips with hooks opening away from each other for holding an elastomeric ring stretched between said hooks.

41. An orthodontic elastomeric ligature ring manipulator comprising a body adapted to be grasped between the thumb and at least one finger of a hand, two prongs projecting lengthwise from said body with their lengths in adjacent relationship, said prongs having tips with hooks opening away from each other for holding an elastomeric ring stretched between said hooks, said hooks of said prong tips being formed by notches in the respective tips and said notch in one of said tips being deeper than said notch in the other of said tips.

42. A orthodontic elastomeric ligature ring manipulator comprising a body having two prongs projecting therefrom in adjacent relationship, said prongs including generally straight shank portions which shank portions of said two prongs are disposed in approximately perpendicularly crossed relationship and said prongs including tip portions having hooks opening away from each other for holding an elastomeric ring extending between said hooks.

43. The manipulator defined in claim 42, in which the prongs include tip portions carried by the shank portions and the shank portion and tip portion of one of the prongs are bent relative to each other to form an offset prong.

44. An orthodontic elastomeric ligature ring manipulator comprising a body having two prongs projecting therefrom in adjacent relationship, said prongs having tips with hooks opening away from each other for holding an elastomeric ring extending between said hooks, one of said prongs being considerably longer than the other of said prongs and having a hook formed by a notch sufficiently shallow that its tip forms a probe extending lengthwise of said longer prong.

45. An orthodontic elastomeric ligature ring manipulator comprising a body having two prongs projecting therefrom in adjacent relationship, said prongs having tips with hooks opening away from each other for holding an elastomeric ring extending between said hooks, and pivot means guiding said prongs for relative movement, each of said prongs including a tip portion and a generally straight shank portion between said tip portion and said body, said shank portions of said two prongs being in mutually substantially perpendicular crossed relationship at a location spaced a substantial distance from the axis of said pivot means and said tip portion and said shank of one of said prongs being disposed in angular relationship to enable said tip portions of said prongs to be disposed in generally parallel relationship when said shank portions of said prongs are in crossed relationship.

46. An orthodontic elastomeric ligature ring manipulator comprising a body having two prongs projecting therefrom in adjacent relationship, pivot means connecting said prongs for relative swinging, said prongs having tips with hooks opening away from each other for holding an elastomeric ring extending between said hooks, and said prongs including shank portions and tip portions, said shank portions being disposed in substantially parallel planes generally perpendicular to the axis of said pivot means and said tip portions being canted at an angle relative to the respective planes of said shank portions for disposing said tip portions in planes substantially parallel to each other and intersecting the planes of said shank portions of said prongs.

* * * * *